(12) United States Patent
Ehlers et al.

(10) Patent No.: US 10,052,016 B2
(45) Date of Patent: Aug. 21, 2018

(54) AUTOMATED CLINICAL EVALUATION OF THE EYE

(71) Applicant: THE CLEVELAND CLINIC FOUNDATION, Cleveland, OH (US)

(72) Inventors: Justis P. Ehlers, Shaker Hts., OH (US); Sunil Srivastava, Shaker Hts., OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 15/369,061

(22) Filed: Dec. 5, 2016

(65) Prior Publication Data
US 2017/0156582 A1    Jun. 8, 2017

Related U.S. Application Data

(60) Provisional application No. 62/262,688, filed on Dec. 3, 2015.

(51) Int. Cl.
*A61B 3/00*     (2006.01)
*G06F 19/00*     (2018.01)
(Continued)

(52) U.S. Cl.
CPC ........... *A61B 3/0025* (2013.01); *A61B 3/102* (2013.01); *A61B 3/1233* (2013.01);
(Continued)

(58) Field of Classification Search
CPC ......... A61B 3/0025; A61B 3/14; A61B 3/102; A61B 3/1241; A61B 3/1233;
(Continued)

(56) References Cited

U.S. PATENT DOCUMENTS

| 7,593,559 B2 | 9/2009 | Toth et al. |
| 9,351,698 B2 | 5/2016 | Dascal et al. |

(Continued)

FOREIGN PATENT DOCUMENTS

| WO | 2013148687 | 10/2013 |
| WO | 2015134641 | 9/2015 |

OTHER PUBLICATIONS

International Search Report corresponding to International Application No. PCT/US2016/0644923, dated Feb. 23, 2017, 14 pages.
Nicholson et al., "Comparison of Wide-Field Fluorescein Angiography and 9-Field Montage Angiography in Uveitis," Am J Opthalmology. Mar. 2014. 157(3):673-677.
Kempen et al., "Fluorscein Angiography versus Optical Coherence Tomography for Diagnosis of Uveitic Macular Edema," Opthalmology. Sep. 2013; 120:1852-1859.
(Continued)

*Primary Examiner* — Jack Dinh
(74) *Attorney, Agent, or Firm* — Tarolli, Sundheim, Covell & Tummino LLP

(57) ABSTRACT

Systems and methods are provided for evaluating an eye of a patient. A first imager interface receives a first image of at least a portion of the eye generated via a first imaging modality, and a second imager interface receives a second image of at least a portion of the eye generated via a second imaging modality. A first feature extractor extracts a first set of numerical features from the first image, with one feature representing a spatial extent of one of a tissue layer, a tissue structure, and a pathological feature. A second feature extractor extracts a second set of numerical features from the second image, with one feature representing one of a number and a location of vascular irregularities within the eye. A pattern recognition component evaluates the first plurality of features and the second plurality of features to assign a clinical parameter to the eye.

9 Claims, 2 Drawing Sheets

(51) Int. Cl.
*A61B 3/14* (2006.01)
*A61B 3/10* (2006.01)
*A61B 3/12* (2006.01)
*G06T 7/00* (2017.01)
*G06K 9/00* (2006.01)
*G16H 10/60* (2018.01)
*G16H 50/20* (2018.01)

(52) U.S. Cl.
CPC .............. *A61B 3/1241* (2013.01); *A61B 3/14* (2013.01); *G06F 19/321* (2013.01); *G06K 9/0061* (2013.01); *G06K 9/00617* (2013.01); *G06T 7/0012* (2013.01); *G16H 10/60* (2018.01); *G16H 50/20* (2018.01); *G06T 2207/10101* (2013.01); *G06T 2207/30041* (2013.01)

(58) Field of Classification Search
CPC .... G06F 19/321; G06F 19/322; G06F 19/345; G06T 7/0012; G06T 2207/10101; G06T 2207/30041; G06K 9/0061; G06K 6/00617
See application file for complete search history.

(56) References Cited

U.S. PATENT DOCUMENTS

2014/0073917 A1   3/2014   Huang et al.
2014/0276025 A1   9/2014   Durbin et al.

OTHER PUBLICATIONS

Campbell et al., "Wide-Field Retinal Imaging in the Management of Noninfectious Posterior Uveitis," Am J Opthalmology. Nov. 2012. 154(5);908-911.

Sim et al., "Patterns of Peripheral Retinal and Central Macula Ischemia in Diabetic Retinopathy as Evaluated by Ultra-widefield Fluorescein Angiography," Jul. 2014. 158(1):144-153.

Wessel et al., "Peripheral retinal ischaemia, as evaluated by ultra-widefield fluorescein angiography, is associated with diabetic macular oedema," Br J Ophthalmology. May 2102. 96(5); 694-698.

Patel et al., "Characterization of Ischemic Index Using Ultra-widefield Fluorescein Angiography in Patients With Focal and Diffuse Recalcitrant Diabetic Macular Edema," Am J Opthalmology. Jun. 2013. 155(6)1038-1044.

Singer et al., "Area of peripheral retinal nonperfusion and treatment response in branch and central retinal vein occlusion," Retina. Sep. 2014. 34(9):1736-1742.

AUTOMATED CLINICAL EVALUATION OF THE EYE

RELATED APPLICATIONS

The present application claims priority to U.S. Provisional Patent Application Ser. No. 62/262,688 filed Dec. 3, 2015 entitled INTEGRATIVE IMAGING BIOMARKER ANALYSIS WITH CORRELATED PHENOTYPIC FEATURES AND OUTCOMES, the entire contents of which being incorporated herein by reference in its entirety for all purposes.

TECHNICAL FIELD

The present invention relates generally to the field of medical decision support, and more particularly to automated clinic evaluation of the eye.

BACKGROUND OF THE INVENTION

Fluorescein and indocyanine green angiography provide ophthalmologists information regarding retinal and choroidal vascular flow. Retinal vascular disease represents a collection of diseases that are among the most frequent causes of blindness in the world. Diabetic retinopathy and retinal vascular occlusive diseases represent the most common of these disorders. Significant recent advances have occurred in the therapeutic options for these conditions including pharmacologics (e.g., steroids, anti-VEGF) and laser (e.g., panretinal photocoagulation, micropulse, focal laser).

Optical coherence tomography (OCT) is an optical signal acquisition and processing method that captures micrometer-resolution, three-dimensional images from within optical scattering media, such as biological tissue. Optical coherence tomography is an interferometric technique, typically employing near-infrared light. The use of relatively long wavelength light allows it to penetrate into the scattering medium. Depending on the properties of the light source, optical coherence tomography has achieved sub-micrometer resolution. Optical coherence tomography systems are employed in diverse applications, including art conservation and diagnostic medicine, notably in ophthalmology where it can be used to obtain detailed images from within the retina and other ophthalmic tissues (e.g., cornea).

SUMMARY OF THE INVENTION

In accordance with an aspect of the present invention, a system is provided for evaluating an eye of a patient. The system includes a processor and a non-transitory computer readable medium storing executable instructions executable by the processor. The instructions include a first imager interface that receives a first image of at least a portion of the eye generated via a first imaging modality and a second imager interface that receives a second image of at least a portion of the eye generated via a second imaging modality. A first feature extractor extracts a first set of numerical features from the first image. At least one of the first set of numerical features represents a spatial extent of one of a tissue layer, a tissue structure, and a pathological feature. A second feature extractor extracts a second set of numerical features from the second image. At least one of the second set of features represents one of a number and a location of vascular or anatomic irregularities within the eye. A pattern recognition component evaluates the first plurality of features and the second plurality of features to assign a clinical parameter to the eye.

In accordance with another aspect of the present invention, a method is provided for evaluating an eye of a patient. A first image of at least a portion of the eye is acquired using a first imaging modality. A second image of at least a portion of the eye is acquired using a second imaging modality that is different than the first imaging modality. A first feature is extracted from the first image. The first feature represents a spatial extent of one of a tissue layer, a tissue structure, and a pathological feature. A second feature is extracted from the second image. The second feature represents one of a number and a location of vascular irregularities within the eye. At least the first feature and the second feature are evaluated at a pattern recognition classifier to assign a clinical parameter to the eye.

In accordance with yet another aspect of the present invention, a method is provided for selecting and applying a therapeutic intervention for a patient having a disorder. A first feature is extracted from a first image. The first feature represents a spatial extent of one of a tissue layer, a tissue structure, and a pathological feature. A second feature is extracted from a second image. The second feature represents one of a number and a location of vascular irregularities within the eye. At least the first feature and the second feature are evaluated at a pattern recognition classifier to select an optimal therapeutic intervention for the patient given the disorder. The selected optimal therapeutic intervention is then applied to the patient.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

In accordance with an aspect of the present invention, an automated quantitative analysis platform is utilized for ophthalmic diagnostics with or without clinical demographics data, including automated or assisted disease diagnosis, tracking of disease progression, evaluation of potential therapies for a given disorder, and identification of optimal therapeutic choice. Examples of potential diseases include diabetic retinopathy, diabetic macular edema, dry age-related macular degeneration, wet age-related macular degeneration, ocular inflammatory disease, radiation retinopathy, and retinal venous occlusive disease. The inventors have determined that combining metrics from various available diagnostic modalities with available clinical information into an integrative analytics model allows for tremendous improvements in diagnostic efficiency, screening platforms, and physician-assisted diagnosis in difficult cases. In one implementation, OCT is employed for evaluation of individual disease features, such as in drug-toxicity and age-related macular degeneration The inventors have further determined that additional clinical variables play critical roles in the disease manifestations and severity of disease burden. Features that are critical may include age, duration of diagnosis, comorbidities, medications, laboratory parameters, and genetic features. The complex interactions between individual imaging features, patterns of disease expression, and clinical variables play a critical role in creating an individualized disease phenotype. This phenotype can only be elucidated through a complex integrative assessment system that would have the potential for not only automated diagnosis, but also individualized therapeutic decision-making support.

Figure 1:
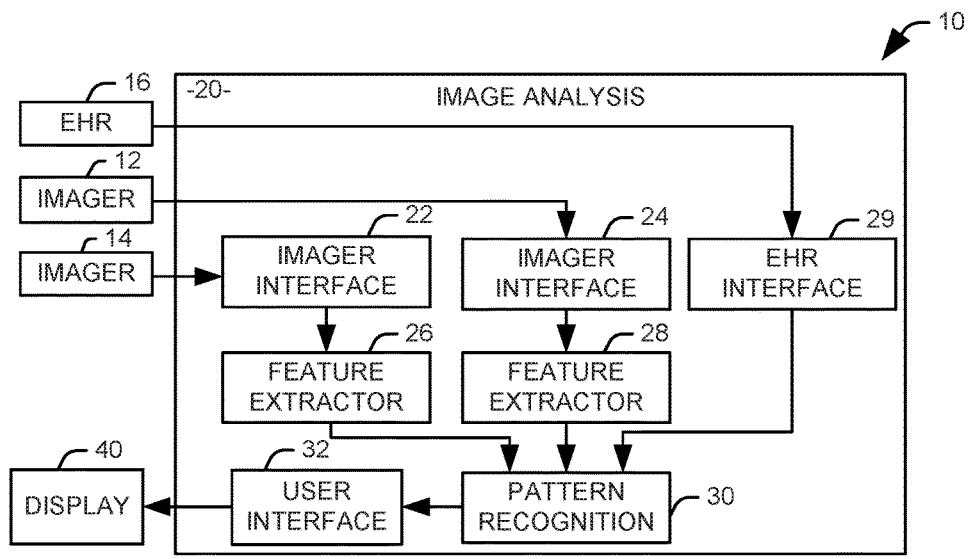
FIG. 1 illustrates a functional block diagram of a system for evaluating an eye of a patient using multiple image modalities.

FIG. 1 illustrates a functional block diagram of a system 10 for evaluating an eye of a patient using multiple image modalities. Specifically, the system can include a first imaging system 12 and a second imaging system 14 each configured to provide an image of the eye. In one implementation, the first imaging system 12 can utilize an imaging modality that is primarily useful for mapping of tissue layers and other structures within the eye, and the second imaging system 14 can use a second imaging modality that is primarily useful for evaluating blood flow within the eye. Examples of appropriate imaging modalities can include optical coherence technology (OCT), fluorescein angiography, indocyanine green angiography, fundus autofluorescence, ultrasonic imaging, photoacoustic imaging, computed tomography (CT), magnetic resonance imaging (MRI), OCT angiography, and Scheimflug imaging. It will further be appreciated that, while the first imaging system 12 and the second imaging system 14 are illustrated as separate structures, it is possible that the two imaging systems could be integrated into a single diagnostic system providing images across multiple imaging modalities. An electronic health records (EHR) database 16 can store information about the patient.

The images from the imaging systems 12 and 14 are provided to an image analysis system 20. It will be appreciated that the image integration system 20 can be implemented as dedicated hardware, machine executable instructions stored on a non-transitory computer readable medium and executed by an associated processor, referred to herein as software, or some combination of dedicated hardware and software components. Further, it will be appreciated that the image analysis system 20 can be implemented as a standalone system working in conjunction with the imaging systems 12 and 14, or as an integral part of one or both imaging systems.

The image analysis system 20 includes a first imager interface 22 configured to receive image data from the first imaging system 12 and a second imager interface 24 configured to receive image data from the second imaging system 14. Each imager interface 22 and 24 communicates with its respective imager to control the acquisition of images and format the image appropriately for additional analysis. The received images can be provided to respective first and second feature extractors 26 and 28.

Each feature extractor 26 and 28 extracts a plurality of numerical features from its received image. It will be appreciated that the features extracted from each image will vary with its associated imaging modality, as imaging modalities have different strengths and weaknesses in the information that they provide. A general category of features can include structural features dealing with the thickness and spatial extent of tissue layers. Examples of such features include a percentage of the layer of interest having at least a specified thickness (e.g., 20 microns, 10 microns, 0 microns), a volume of the layer of interest, a percentage of the area of the scan for which the layer of interest is absent, average thickness in defined regions of a tissue layer, and the volume of lesions within the tissue. One or more similarity values can be extracted based on a similarity of the spatial distribution of layer thickness to spatial patterns of pathologies or other clinically relevant events. For some disorders, the analysis of structural features might be limited to specific layers of tissue, such as one or more retinal sublayers. The inventors have provided an automated means for extracting these features, for example, from spatial domain OCT images, in application Ser. No. 13/850,846 titled Volumetric Analysis of Pathologies (now issued as U.S. Pat. No. 9,299,139). The entirety of this patent is hereby incorporated by reference for all purposes.

Another set of features can focus on the presence, location, and extent of enclosed pathologic variables (e.g., retinal edema, macular hole, subretinal fluid, atrophy) within the eye or around specific tissue layers, such as a volume of the fluid and whether it is subretinal or intraretinal. Yet another set of features can focus on the number, location, and spatial extent of vascular irregularities such as microaneurysms, ischemia, neovascularization, and vessel leakage. For example, extracted features can include a number of each vascular irregularity in each of a plurality of zonal locations, such as posterior, mid-peripheral, and far-peripheral, a total number of each vascular irregularity, an area affected by ischemia or proportion of an area affected by ischemia, an area of leakage or proportion of area of leakage, the presence of perivascular leakage, and a percentage of vascular tree associated with perivascular leakage. The inventors have provided an automated means for indentifying these vascular irregularities, for example, from angiography images, in application Ser. No. 14/847,772 titled Automated Analysis of Angiographic Images (now published as U.S. Published Patent Application No. 2016/0071266). In addition, an EHR interface 29 can retrieve biometric parameters representing the patient from the EHR database 16. It will be appreciated that, as used herein, "biometric parameters" can include measurements of vital parameters of the patient, such as blood levels, weight, blood pressure, and similar values, reported behavioral data, clinical data, such as diagnoses of other disorders and family history, and demographic data, such as age, sex, race, occupation, and city of employment or residence. The retrieved biometric parameters can represent, for example, any of age, blood glucose level, HbA1c level, reported cigarette usage, gender, medical history, body mass index, weight, family history, medication usage, and hemoglobin levels The features extracted from the first and second images and the biometric parameters retrieved from the EHR 16 are provided to a pattern recognition component 30 to select an appropriate clinical class according to the extracted features. It will be appreciated that a clinical parameter, as used herein, can be a categorical parameter, representing a specific disorder or grade of progression of the disorder, an improvement, degradation, or lack of change in a condition, or a clinical treatment that is likely to be useful for the region of interest. Alternatively, the clinical parameter can be a continuous parameter, such as a metric representing a likelihood that a given treatment will be successful, a degree of improvement or degradation in a condition, a likelihood that a particular disorder is present, or an index indicating the prevalence of various localized disorders. In one implementation, the number and/or locations of localized disorders can be used as features in subsequent assignment of a clinical parameter.

In one implementation, the pattern recognition component 30 can comprise one or more pattern recognition classifiers, each of which utilize the extracted features or a subset of the extracted features to determine an appropriate clinical parameter for the occupant. Where multiple classifiers are used, an arbitration element can be utilized to provide a coherent result from the plurality of classifiers. Each classifier is trained on a plurality of training images representing various classes of interest. The training process of the a given classifier will vary with its implementation, but the training generally involves a statistical aggregation of training data from a plurality of training images into one or more parameters associated with the output class. Any of a variety of optimization techniques can be utilized for the classification algorithm, including support vector machines, self-organized maps, fuzzy logic systems, data fusion processes, ensemble methods, rule based systems, or artificial neural networks.

For example, a support vector machine (SVM) classifier can process the training data to produce functions representing boundaries in a feature space defined by the various attributes of interest. Similarly, an artificial neural network (ANN) classifier can process the training data to determine a set of interconnection weights corresponding to the interconnections between nodes in its associated the neural network.

A SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. A rule-based classifier applies a set of logical rules to the extracted features to select an output class. Generally, the rules are applied in order, with the logical result at each step influencing the analysis at later steps.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

In another implementation, the pattern recognition component 30 can include a regression model configured to provide calculate a parameter representing a likelihood that the patient has a given disorder, a likelihood that a patient will respond to a specific therapeutic procedure, or an extent to which a patient is affected by a given disorder. In yet another implementation, the pattern recognition component 30 can perform a sensitivity analysis using the model, such that a magnitude of the effect of one or more features on the at least one parameter can be determined.

In one implementation, the pattern recognition component 30 can comprise one or more pattern recognition classifiers, each of which utilize the extracted features or a subset of the extracted features to determine an appropriate clinical parameter for the occupant. Where multiple classifiers are used, an arbitration element can be utilized to provide a coherent result from the plurality of classifiers. Each classifier is trained on a plurality of training images representing various classes of interest. The training process of the a given classifier will vary with its implementation, but the training generally involves a statistical aggregation of training data from a plurality of training images into one or more parameters associated with the output class. Any of a variety of optimization techniques can be utilized for the classification algorithm, including support vector machines, self-organized maps, fuzzy logic systems, data fusion processes, ensemble methods, rule based systems, or artificial neural networks. In one implementation, the outcome class can represent a predicted range of outcomes for the patient given the application of the therapeutic procedure. This can range from a binary "good" and "bad" to a plurality of graduations of expected success. From the provided features, an outcome class is selected and a confidence in the selected result can be calculated. Results falling below a threshold confidence value can be rejected.

In one example, a support vector machine (SVM) classifier can process the training data to produce functions representing boundaries in a feature space defined by the various attributes of interest. A SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries.

Similarly, an artificial neural network (ANN) classifier can process the training data to determine a set of interconnection weights corresponding to the interconnections between nodes in its associated the neural network. An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge.

In another implementation, the pattern recognition component 30 can include a regression model configured to provide calculate a parameter representing a likelihood that the patient has a given disorder, a likelihood that a patient will respond to a specific therapeutic procedure, or an extent to which a patient is affected by a given disorder. In yet another implementation, the pattern recognition component 30 can perform a sensitivity analysis using the model, such that a magnitude of the effect of one or more features on the at least one parameter can be determined. The clinical parameter is then displayed to a user via a user interface 32 at an associated display 40. In one example, the first and second images can be provided to the user as well, with appropriate tools for viewing and manipulating the images.

In one implementation, the first imaging modality is optical coherence tomography (OCT), for example, spectral domain OCT, and the second imaging modality is angiography, such as fluorescein angiography, indocyanine green angiography, and OCT angiography. The inventors have determined that through the use of multiple automated image assessment tools/technology for OCT, angiography to discover vascular irregularities, automated anterior chamber cell measurements from the OCT imaging, and OCT-angiography combined with each other and/or biometric parameters. The biometric parameters can represent, for example, any of age, blood glucose level, HbA1c level, reported cigarette usage, gender, medical history, body mass index, weight, family history, medication usage, and hemoglobin levels.

In one implementation, the system 10 can be used for diagnosis of disorders of a patient's eye, such that the pattern recognition classifier provides a general disease class for the patient, each representing either one of the plurality of disorders or a disease-free state. In another implementation, the pattern recognition classifier 30 evaluates the patient for a single disorder, with either a binary normal/abnormal classification or a set of classes reach representing a grade of severity of the pathology.

In one example, the pattern recognition system 30 can identify diabetic retinopathy with or without diabetic macular edema. Specifically, the pattern recognition system 30 can classify the patient in one of nine classes: normal, mild diabetic retinopathy without diabetic macular edema, moderate diabetic retinopathy without diabetic macular edema, severe diabetic retinopathy without diabetic macular edema, proliferative diabetic retinopathy without diabetic macular edema, mild diabetic retinopathy with diabetic macular edema, moderate diabetic retinopathy with diabetic macular edema, severe diabetic retinopathy with diabetic macular edema, and proliferative diabetic retinopathy with diabetic macular edema. It will be appreciated that the classes are merely exemplary, and, for example, other disease grades could be selected for different applications.

To this end, the first feature extractor 26 can extract features from a spatial domain OCT signal, including a volume of intraretinal fluid, which can be zero, and a volume of subretinal fluid, which can be zero. From one or more angiography images, the second feature extractor 28 can extract features including each of a number of microaneurysms in the eye, a number of microaneurysms in the posterior pole, a number of microaneurysms in the superior field, a number of microaneurysms in the inferior field, a volume of ischemia in the eye, a volume of ischemia in the posterior pole, a volume of ischemia in the superior field, a volume of ischemia in the inferior field, a volume of ischemia within the macular region, a volume of vascular leakage in the eye, a volume of vascular leakage in the posterior pole, a volume of vascular leakage in the superior field, and a volume of vascular leakage in the inferior field. Relevant biometric parameters for use in the classification can include a diagnosis of diabetes, a length of time the patient has had diabetes, current and historical HbA1c levels, and current and historical glucose levels.

In another example, the pattern recognition system 30 can identify macular degeneration, for example, age related macular degeneration. Macular degeneration is one of the leading causes of blindness in the world. Early detection of macular degeneration is critical. Utilizing automated detection techniques to identify deflections in the retinal pigment epithelium consistent with drusen on OCT combined with clinical demographics with patient age and lack of leakage on angiography and lack of fluid on OCT could confirm the diagnosis of dry macular degeneration. Automated ellipsoid zone mapping could identify areas of atrophy to facilitate grading/staging of the severity of macular disease. Automated detection of intraretinal or subretinal fluid, combined with sub-retinal pigment epithelium pathology and potential leakage on FA, vascular flow on OCT-A, and potential hemorrhage on fundus photos could confirm a diagnosis of wet macular degeneration.

To this end, the pattern recognition classifier 30 can classify the patient as having no macular degeneration, dry macular degeneration without geographic atrophy, dry macular degeneration with geographic atrophy, and wet macular degeneration. To this end, the first feature extractor 26 can extract features from a spatial domain OCT signal, including a volume of intraretinal fluid, which can be zero, a volume of subretinal fluid, which can be zero, a number and total area of deflections to the retinal pigment epithelium (RPE), and a thickness or volume of one or more retinal layer within the ellipsoid zone. The second feature extractor 28 can extract features including a volume of vascular leakage in the eye. Relevant biometric parameters for use in the classification can include an age of the patient, and various parameters quantifying current and historical smoking habits of the patients.

In still another example, the pattern recognition system 30 can identify drug-related retinal toxicity, such as from plaquenil. Early detection of plaquenil toxicity is crucial. Subtle changes on the OCT retinal layers are among the earliest findings but are often overlooked. Automated assessment of outer retinal layers, particularly within the ellipsoid zone, and detection of subclinical alterations, will be critical for early disease detection, and can be combined with patients' current medication list to facilitate identifying the potential source of the toxicity.

In yet another example, the pattern recognition system 30 can identify retinal vascular occlusions. Retinal vascular occlusions are a frequent cause of visual disability. These tend to have distinct patterns of distribution of disease, and are thus amenable to automated analysis. Sectoral or hemispheric involvement of specific vascular features such as leakage or ischemia may facilitate automated diagnosis. Additionally sectoral distribution of retinal fluid on OCT with automated detection could facilitate diagnosis. Distinguishing features such as increased inner retinal reflectivity in retinal artery occlusions may help to discriminate artery and vein occlusions on OCT. Systemic and ocular factors may help to facilitate diagnosis through identification of significant risk factors, such as hypertension, diabetes, or glaucoma.

To this end, the pattern recognition classifier 30 can classify the patient as having no vascular occlusions, venous occlusions with macular edema, venous occlusions without macular edema, and arterial occlusions. To this end, the first feature extractor 26 can extract features from a spatial domain OCT signal, including a volume of intraretinal fluid, which can be zero, and a volume of subretinal fluid, which can be zero. The second feature extractor 28 can extract features including a volume of vascular leakage in the eye, a volume of vascular leakage near veins, a volume of vascular leakage near arteries, a volume of vascular leakage in various defined regions to monitor sections of the eye, a volume of perivascular leakage, and a volume of the macular region affected by ischemia. Relevant biometric parameters for use in the classification can include a current and historical blood pressure of the patient, a current and historical intraocular pressure of the patient, and various parameters quantifying the presence and progression of glaucoma and diabetes.

In a further example, the pattern recognition system 30 can identify ocular inflammatory disease. To this end, the first feature extractor 26 can extract features from a spatial domain OCT signal, including a volume of intraretinal fluid, which can be zero, and a volume of subretinal fluid, which can be zero, at least one parameter representing vitreous reflectance, and at least one parameter reflecting a prevalence of cells within the anterior chamber. The second feature extractor 28 can extract features including a volume of vascular leakage in the eye and a volume of the eye affected by ischemia. Relevant biometric parameters for use in the classification can include various parameters quantifying the presence and progression of systemic inflammatory disorders.

In another implementation, the system 10 can be used for disease surveillance and monitoring. Longitudinal assessment of alterations in integrative pattern parameters and features may directly change prognosis and guide monitoring frequency. This can include disease regression, such as resolution of macular edema, reduction in diabetic retinopathy severity scale, and inflammatory mediators. Accordingly, the system 10 can be utilized to monitor conditions undergoing active treatment for disorders such as age-related macular degeneration, diabetic macular edema, ocular inflammatory disease, and retinal vascular occlusive disease. Additional clinical features could be utilized within the overall integrative assessment platform such as age, underlying diagnosis, duration of diagnosis, and visual acuity.

The management of intraocular inflammation is a critical component to multiple ophthalmic conditions. There is a very wide spectrum in disease response to therapy, optimal therapeutic choice, and disease manifestations. Assimilating the numerous parameters of ocular inflammation including automated OCT-based assessment of anterior chamber inflammation, quantitative metrics of angiography, OCT-based assessment of retinal layer integrity, and OCT-based assessment of retinal fluid, allows for optimization of follow-up and disease management for therapeutic response. Additionally, integrating this information with underlying diagnosis, patient age, and medications provides additional integrative data.

In one example, the pattern recognition classifier 30 can track disease progression or response to therapy with four classes representing an improved condition, a stable condition, a worsened conditioned, and a greatly worsened condition. Alternatively, a continuous numerical parameter representing disease progression can be assigned. It will be appreciated that the features in this instance are longitudinal and may be expressed as a time series of values, representing measurements over time. The parameters extracted at the first feature extractor 26 can include an ellipsoid zone (EZ) loss, particularly EZ-RPE volume, thickness in the EZ as determined by en face EZ mapping, changes in EZ atrophy on EZ mapping, changes in retinal volume, changes in the volume of intraretinal fluid, and changes the volume of subretinal fluid. The second feature extractor 28 can extract features including a change in the volume of vascular leakage in the eye and a change in the volume of the eye affected by ischemia. Relevant biometric parameters for use in the classification can include various parameters quantifying visual acuity, systemic parameters, comorbidities, severity of diabetes, age, severity of hypertension, and smoking history.

In another implementation, the system 10 can be used for individualized therapeutic decision-making. Numerous disease conditions exist that have multiple therapeutic options, such as anti-VEGF therapy vs steroids for diabetic macular edema. Numerous systemic immunosuppressants and local therapy options exist for ocular inflammatory diseases. Utilizing integrative pattern analysis of both quantitative and regional activity signatures, such as the location in the retina, on multi-modal imaging modalities with or without combination to clinical demographics provides a therapeutic decision support system for identifying features that may be a marker for more optimal therapeutic choice.

In one example, the system 10 is applied to diabetic macular edema. Diabetic macular edema is an incredibly heterogeneous condition that has multiple therapeutic options and many more under clinical trials. Currently, there are no indicators for which therapeutic would be best for a patient. Some patients have a more inflammatory phenotype that responds to steroids. Others appear to have a more vascular endothelial growth factor (VEGF) driven phenotype that responds to anti-VEGF therapy. Still others don't respond well to either modality. Currently the only way to assess what works is to try a therapy and assess response. Utilizing the integrative pattern assessment platform provided by the system 10, selected variables from multi-modal imaging are integrated to create an imaging fingerprint of the disease and combined with clinical features within the learning algorithm platform to provide a predictive model would allow clinicians to examine the current disease features, such as primary location of leakage, extent of leakage, presence of fluid parameters, and determine the most likely driving force for the disease, that is—inflammation, VEGF, or an additional alternate pathway. The physician can then select the optimal therapeutic based on that decision-support, creating a more rapid and individualized treatment paradigm. This pattern could be a surrogate for expression levels of various disease factors.

In one example, the pattern recognition classifier 30 can assign the patient to one of four classes representing a likely response to steroids, a likely response to anti-VEGF therapy, a likely response to both treatments, or a likely response to neither treatment. The parameters extracted at the first feature extractor 26 can include a ratio of the volume of intraretinal fluid to the volume of subretinal fluid. The second feature extractor 28 can extract features including a change in the volume of vascular leakage in the eye, the volume of the eye affected by ischemia, the volume of the macula affected by ischemia, a ratio of the vascular leakage at the posterior pole to the volume of vascular leakage in the eye, a ratio of the perivascular leakage volume to the total volume of vascular leakage in the eye, the volume of vascular leakage in various sectors of the eye, as well as ratios of each of these volumes to a total volume of vascular leakage in the eye, the volume affected by ischemia in various sectors of the eye, as well as ratios among these volumes, and a number of microaneurysms in the eye. When possible, the response of any of these parameters to a single anti-VEGF injection can also be measured and utilized in the analysis. Relevant biometric parameters for use in the classification can include various parameters quantifying a duration for which the patient has had the disease, a severity of diabetes, if any, and age.

Figure 2:
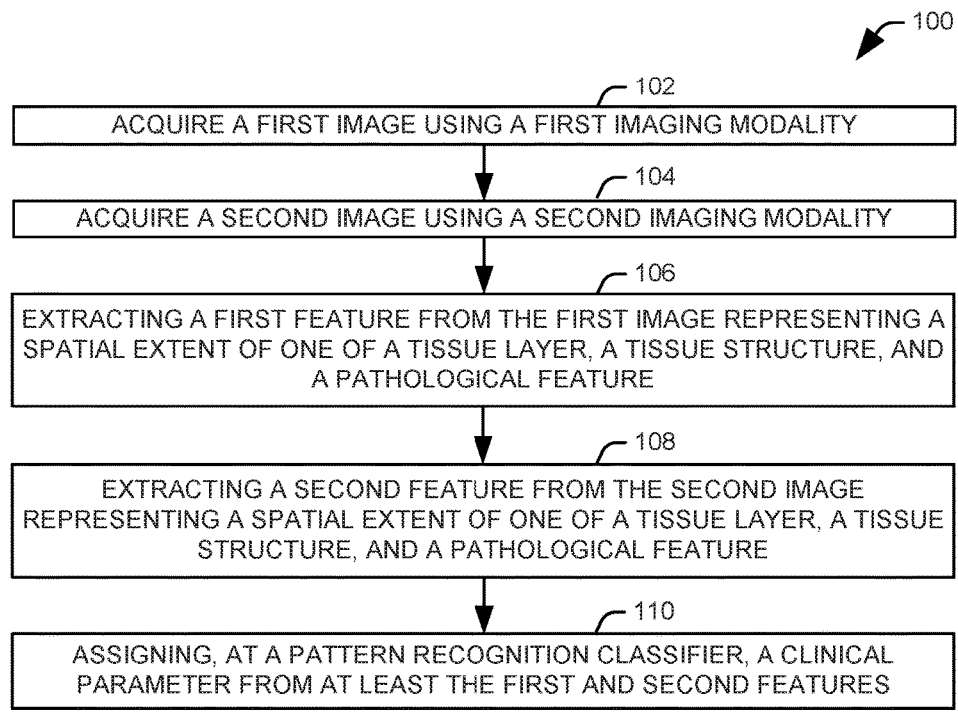
FIG. 2 illustrates a method for evaluating an eye of a patient from image features extracted from multiple modalities.
Figure 3:
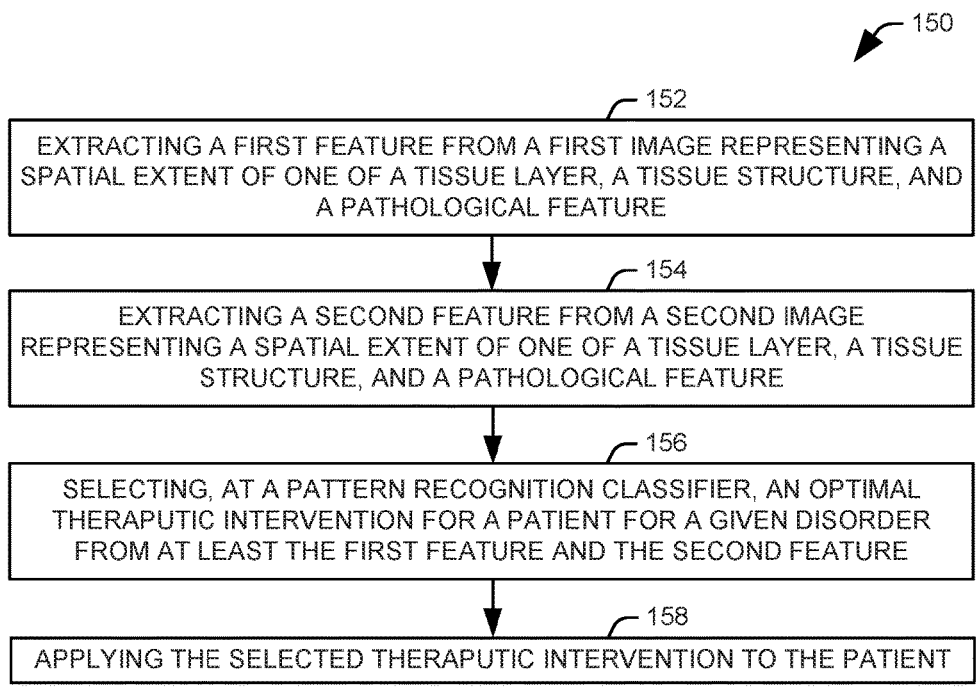
FIG. 3 illustrates a method for selecting and applying a therapeutic intervention for a patient having a disorder.

In view of the foregoing structural and functional features described above, a method in accordance with various aspects of the present invention will be better appreciated with reference to FIGS. 2 and 3. While, for purposes of simplicity of explanation, the methods of FIGS. 2 and 3 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect the present invention.

FIG. 2 illustrates a method 100 for evaluating an eye of a patient from image features extracted from multiple modalities. At 102, a first image of at least a portion of the eye is acquired using a first imaging modality. In one implementation, the first imaging modality is optical coherence tomography. At 104, a second image of at least a portion of the eye is acquired using a second imaging modality that is different than the first imaging modality. At 106, a first feature is extracted from the first image, representing a spatial extent of one of a tissue layer, a tissue structure, and a pathological feature. Examples can include volumes or areas of fluid or lesions, numbers, sizes, and locations of deflections of tissue layers, as well as tissue layer thicknesses and volumes, particularly in regions of clinical interest such as the ellipsoid zone.

At 108, a second feature is extracted from the second image, representing one of a number and a location of vascular irregularities within the eye. Examples can include numbers of microaneurysms, leakage sites, sites of neovascularization, and areas of ischemia within the eye or within various defined regions of the eye, as well as parameters derived from these values. At least the first feature and the second feature are evaluated at a pattern recognition classifier at 110 to assign a clinical parameter to the eye. As described previously, the clinical parameter can be a categorical or continuous representing a specific disorder or grade of progression of the disorder, an improvement, degradation, or lack of change in a condition, or a clinical treatment that is likely to be useful for the region of interest. It will be appreciated that the features to be evaluated can include multiple features extracted from each image, features extracted from additional images, and biometric parameters associated with the patient. The clinical parameter can be provided to a user through appropriate output means, such as a display.

FIG. 3 illustrates a method 150 for selecting and applying a therapeutic intervention for a patient having a disorder, for example, any of diabetic retinopathy, diabetic macular edema, dry age-related macular degeneration, wet age-related macular degeneration, ocular inflammatory disease, radiation retinopathy, and retinal venous occlusive disease. At 152, a first feature is extracted from a first image, representing a spatial extent of one of a tissue layer, a tissue structure, and a pathological feature. In one example, the first feature can be a ratio of a volume of intraretinal fluid to a volume of subretinal fluid. At 154, a second feature is extracted from a second image, representing one of a number and a location of vascular irregularities within the eye. In one example, the second feature can be one of a plurality of features comprising a regional volume of vascular leakage for each a plurality of defined regions within the eye and/or ratios of each regional volume to a total volume of vascular leakage. In one implementation, the first image can be acquired via a first imaging modality, and the second image can be acquired via a second imaging modality that is different than the first imaging modality.

At 156, at least the first feature and the second feature are evaluated at a pattern recognition classifier to select an optimal therapeutic intervention for the patient given the disorder. In the example of diabetic macular edema, the therapeutic interventions to be selected between can include one of steroids and an anti-VEGF therapy, with the classifier selecting between a steroid class, an anti-VEGF class, and a class representing patients for whom neither therapy is expected to be effective. It will be appreciated that the features to be evaluated can include multiple features extracted from each image, features extracted from additional images, and biometric parameters representing any of the age, blood glucose level, HbA1c level, reported cigarette usage, gender, medical history, body mass index, weight, family history, medication usage, and hemoglobin levels of the patient. The selected optimal therapeutic intervention is then applied to the patient at 158.

Figure 4:
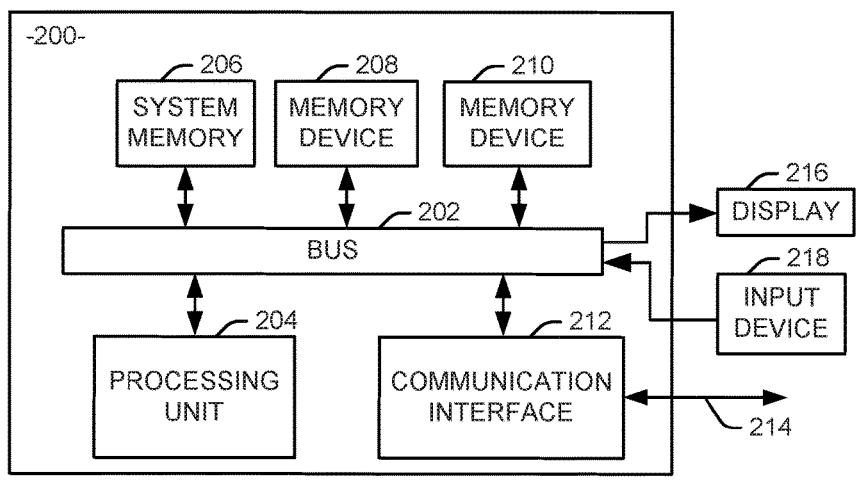
FIG. 4 is a schematic block diagram illustrating an exemplary system of hardware components capable of implementing examples of the systems and methods disclosed herein.

FIG. 4 is a schematic block diagram illustrating an exemplary system 200 of hardware components capable of implementing examples of the systems and methods disclosed in FIGS. 1-3, such as the imaging system illustrated in FIG. 1. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand-alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of a diagnostic and decision support system in accordance with the present invention. Computer executable logic for implementing the composite applications testing system resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to any medium that participates in providing instructions to the processing unit 204 for execution, and it will be appreciated that a computer readable medium can include multiple computer readable media each operatively connected to the processing unit.

From the above description of the invention, those skilled in the art will perceive improvements, changes, and modifications. Such improvements, changes, and modifications within the skill of the art are intended to be covered by the appended claims.

Having described the invention, we claim:

1. A system for evaluating an eye of a patient comprising:
   a processor; and
   a non-transitory computer readable medium storing executable instructions executable by the processor comprising:
   a first imager interface that receives a first image of at least a portion of the eye generated via a first imaging modality;
   a second imager interface that receives a second image of at least a portion of the eye generated via a second imaging modality;
   a first feature extractor that extracts a first set of numerical features from the first image, at least one of the first set of numerical features representing a spatial extent of one of a tissue layer, a tissue structure, and a pathological feature;
   a second feature extractor that extracts a second set of numerical features from the second image, at least one of the second set of features representing one of a number and a location of vascular irregularities within the eye; and
   a pattern recognition component that evaluates the first plurality of features and the second plurality of features to assign a clinical parameter to the eye.

2. The system of claim 1, wherein the pattern recognition component evaluates the first set of features, the second set of features, and a set of biometric parameters associated with the patient to assign a clinical parameter to the eye.

3. The system of claim 2, the set of biometric parameters comprising parameters representing two or more of age, blood glucose level, HbA1c level, reported cigarette usage, gender, medical history, body mass index, weight, family history, medication usage, and hemoglobin levels.

4. The system of claim 1, wherein the first imaging modality is optical coherence tomography, and the second imaging modality is one of fluorescein angiography, indocyanine green angiography, and OCT angiography.

5. The system of claim 1, wherein the at least one of the first set of numerical features comprises one of a volume of an intraretinal fluid and a volume of a subretinal fluid.

6. The system of claim 1, wherein the at least one of the second set of features comprises at least one of a number of microaneurysms in the eye, a volume of vessel leakage in the eye, and a volume of the eye affected by ischemia.

7. The system of claim 1, wherein the at least one of the second set of features comprises a number of a given vascular irregularity within each of a plurality of defined regions within the eye.

8. The system of claim 1, wherein the assigned clinical parameter represents an optimal therapeutic intervention for a disorder associated with the patient.

9. The system of claim 1, wherein the assigned clinical parameter represents an improvement, degradation, or lack of change in an existing disorder.

* * * * *